(12) United States Patent
Lin et al.

(10) Patent No.: US 8,153,387 B2
(45) Date of Patent: Apr. 10, 2012

(54) METHOD FOR IMMOBILIZING GLYCOPROTEIN

(75) Inventors: Chun-Cheng Lin, Hsinchu (TW); Mu-Lin Chen, Hsinchu (TW); Po-Chiao Lin, Hsinchu (TW); Yu-Ju Chen, Hsinchu (TW); Shu-Hua Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 442 days.

(21) Appl. No.: 12/490,953

(22) Filed: Jun. 24, 2009

(65) Prior Publication Data

US 2010/0190966 A1  Jul. 29, 2010

(30) Foreign Application Priority Data

Jan. 23, 2009  (TW) ............................... 98102767 A (51) Int. Cl.
*G01N 33/53* (2006.01)

(52) U.S. Cl. ............ 435/7.21; 435/7.1; 436/1; 436/501; 436/518; 424/9.1; 424/520; 422/1; 422/50; 530/300; 530/350

(58) Field of Classification Search ........................ None
See application file for complete search history.

(56) References Cited

U.S. PATENT DOCUMENTS

| 5,527,713 A | * | 6/1996 | Bolton et al. | ................. 436/529 |
| 6,231,982 B1 | * | 5/2001 | Wang | ............................ 428/407 |
| 6,649,419 B1 | * | 11/2003 | Anderson | ..................... 436/526 |

* cited by examiner

*Primary Examiner* — Lisa Cook (74) *Attorney, Agent, or Firm* — Muncy, Geissler, Olds & Lowe, PLLC (57) ABSTRACT

A method for immobilizing glycoprotein is disclosed. A surface is provided. Next, a boronic acid is contacted to the surface. The boronic acid is represented as Y—R—B—(OH)$_2$ and includes a boronic acid group (B—(OH)$_2$), a linker R, and a functional group Y, in which the boronic acid is bonded to the surface via the functional group Y. A glycoprotein is contacted to the boronic acid, wherein two spatially adjacent hydroxyl groups of a carbohydrate chain form a boronate ester with the boronic acid group of the boronic acid to immobilize the glycoprotein. The goal of site-specific and covalent protein immobilization without interfering the binding affinity of an antibody to antigen may be thus achieved with the reaction of boronic acid and the carbohydrate chain of Fc region.

22 Claims, 11 Drawing Sheets

METHOD FOR IMMOBILIZING GLYCOPROTEIN

This application is a continuation of foreign application number 98102767 filed Jan. 23, 2009 in Taiwan.

BACKGROUND OF THE INVENTION

1. Field of the Invention

The present invention relates to a method for immobilizing glycoprotein, and more particularly to a method for immobilizing glycoprotein by forming covalent bonding with two spatially adjacent hydroxyl groups of a carbohydrate chain.

2. Description of the Prior Art

In the development of protein microarray, the accessibility of surface protein active site and stability may be significantly influenced by its orientation on the solid surface. Therefore, various site-specific immobilization strategies have been developed.

Due to tight and specific epitope affinities, antibodies have been widely used in immunoaffinity extraction, targeted therapeutic delivery, enzyme-linked immunosorbent assays, and diagnostic arrays.

Traditionally, antibodies have been modified at lysine, arginine, aspartate, and glutamate residues by random amide bond conjugation or Schiff base formation. However, such random conjugation often reduces antibody function to a point that is inadequate for the desired application.

In addition, antibody binding proteins, e.g. protein G and protein A, are commonly used to anchor/immobilize antibody via the Fc (Fragment, crystallizable) region in a site-specific manner for exposing the Fab (Fragment, antigen-binding) region in an efficient way. However, the aforementioned non-covalent coupling between the antibody binding protein and antibody is likely subjected to dissociation caused by environmental factors such as pH value, salinity, and temperature.

Therefore, it is a now current goal to develop a method for immobilizing glycoprotein which is site-specific and covalent protein immobilization without interfering the binding affinity of an antibody to antigen.

SUMMARY OF THE INVENTION

The present invention is directed to provide a method for immobilizing glycoprotein via reaction of boronic acid and carbohydrate chain with advantages of site-specific and covalent protein immobilization without interfering the binding affinity of an antibody to antigen.

According to an embodiment of the present invention, a method for immobilizing glycoprotein comprises providing a surface; contacting a boronic acid to the surface, wherein the boronic acid is represented as Y—R—B—(OH)$_2$ and includes a boronic acid group B—(OH)$_2$, a linker R, and a functional group Y, in which the boronic acid is bonded to the surface via the functional group Y; and contacting a glycoprotein to the boronic acid, wherein two spatially adjacent hydroxyl groups of a carbohydrate chain form a boronate ester with the boronic acid group of the Y—R—B—(OH)$_2$ to immobilize the glycoprotein.

Other advantages of the present invention will become apparent from the following description taken in conjunction with the accompanying drawings wherein are set forth, by way of illustration and example, certain embodiments of the present invention.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1A:
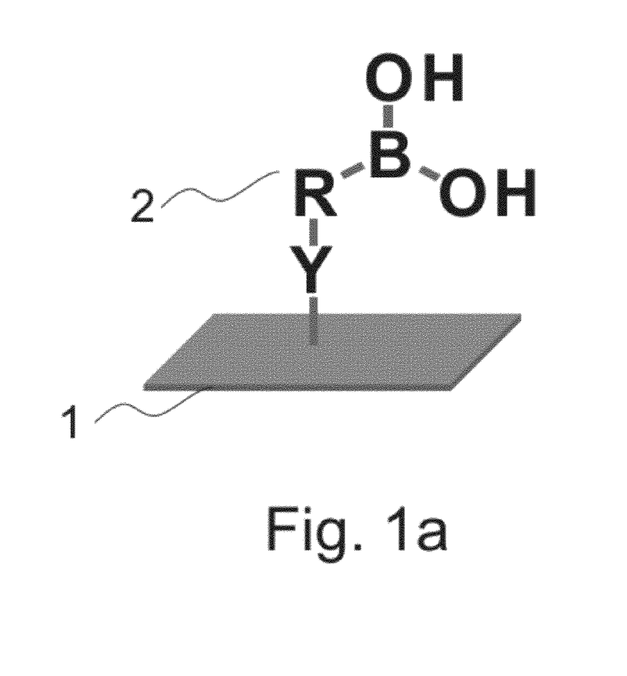
FIG. 1a to FIG. 1c are schematic diagrams illustrating a method for immobilizing glycoprotein according to an embodiment of the present invention.
Figure 1B:
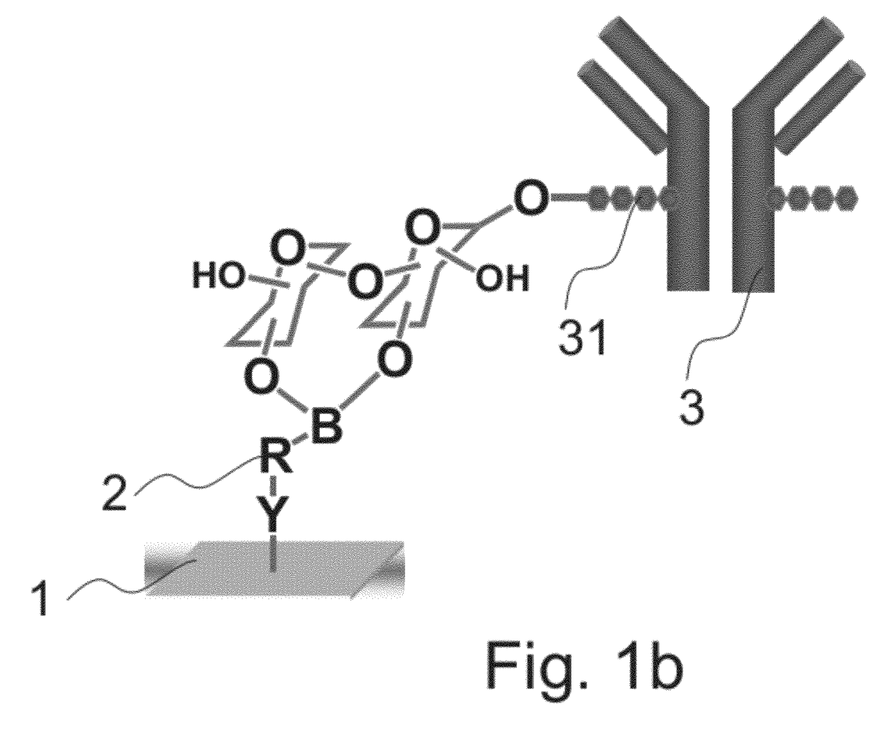

FIGS. 1a and 1b illustrate a method for immobilizing glycoprotein according to an embodiment of the present invention. As illustrated in FIG. 1a, first, a surface 1 is provided. A boronic acid 2 is then contacted to the surface 1, wherein the boronic acid 2 is represented as Y—R—B—(OH)$_2$ and includes a boronic acid group B—(OH)$_2$, a linker R bonded to the boronic acid, and a functional group Y bonded to the linker R, in which the boronic acid 2 is bonded to the surface 1 via the functional group Y as illustrated in FIG. 1a.

The linker R of the boronic acid 2 includes an alkyl group, an alkoxy group, an alkyl ether group, an alkyl sulfide, a cycloalkyl group, a heterocyclyl group, an aryl group or a heteroaryl group. In an embodiment, the linker R further includes an auxiliary substituent X substituted phenyl ring for modulating the electrons in the boronic acid group.

In phenyl ring of the linker R, the auxiliary substituent X may comprise an boronic acid binding facilitator such as an electron-withdrawing group (e.g. a halide group, carboxyl group, nitrosyl group) or a boroxine inhibiting group (e.g. hydroxymethyl group) for maintaining boronic acid activity.

In phenyl ring of the linker R, the auxiliary substituent X may comprise a second interaction donor or acceptor, such as covalent bond, hydrogen bond and chelating group.

In addition, the linker R may further include an amide group linking to the phenyl ring. The amide group in the linker R may be used for modulating the length of linker R via amide bond formation.

Furthermore, examples of the surface 1 include a solid support, a nanoparticle or a biochip, e.g. a protein chip. The functional group Y may be a member selected from the group consisting an amine, a hydrazide (—CO—NH—NH$_2$), an amine oxide (—O—NH$_2$), a thiol (—SH), an alkyne, an azide, a triaryl phosphine, an alkene, a diene, a cysteine, a thioester, a diazo, a diazirine, a benzophenone, and a diazonium. The boronic acid 2 may be bonded to the surface 1 via Schiff base formation, amide bond formation, Staudinger ligation, 1,3-dipolar cycloaddition, Diels-alder [4+2] reaction, native chemical ligation, photo induced carbene immobilization, or photo induced nitrene immobilization.

A glycoprotein is then contacted to the boronic acid 2. The glycoprotein is a protein containing at least one carbohydrate chain by definition, and the carbohydrate chains may be site-specific for achieving site-specific immobilization.

The glycoprotein may be lectin, for example, ricin or RCA$_{120}$, in which the carbohydrate chains located far from the active site for achieving site-specific immobilization. The glycoprotein may be glycosylated enzyme, for example, glucose oxidase, horseradish peroxidase, RNase B, aminoacylase from *Aspergillus melleus*, chloroperoxidase from *Caldariomyces fumago*, and phytase from *Aspergillus ficuum*, in which the carbohydrate chains may be either located or long enough to be far from the active site for achieving site-specific immobilization.

The glycoprotein may be an antibody 3 with Fc region containing a carbohydrate chain 31 in this embodiment, for example. As illustrated in FIG. 1b, two spatially adjacent hydroxyl groups of a carbohydrate chain 31 in the Fc region of the antibody 3 form a boronate ester with the boronic acid group of the boronic acid 2; therefore, the antibody 3 is bonded to the boronic acid 2 and the antibody 3 is thus immobilized. In a preferred embodiment, the boronate ester is formed with two spatially adjacent hydroxyl groups of the carbohydrate chain 31 and the boronic acid 2.

Figure 1C:
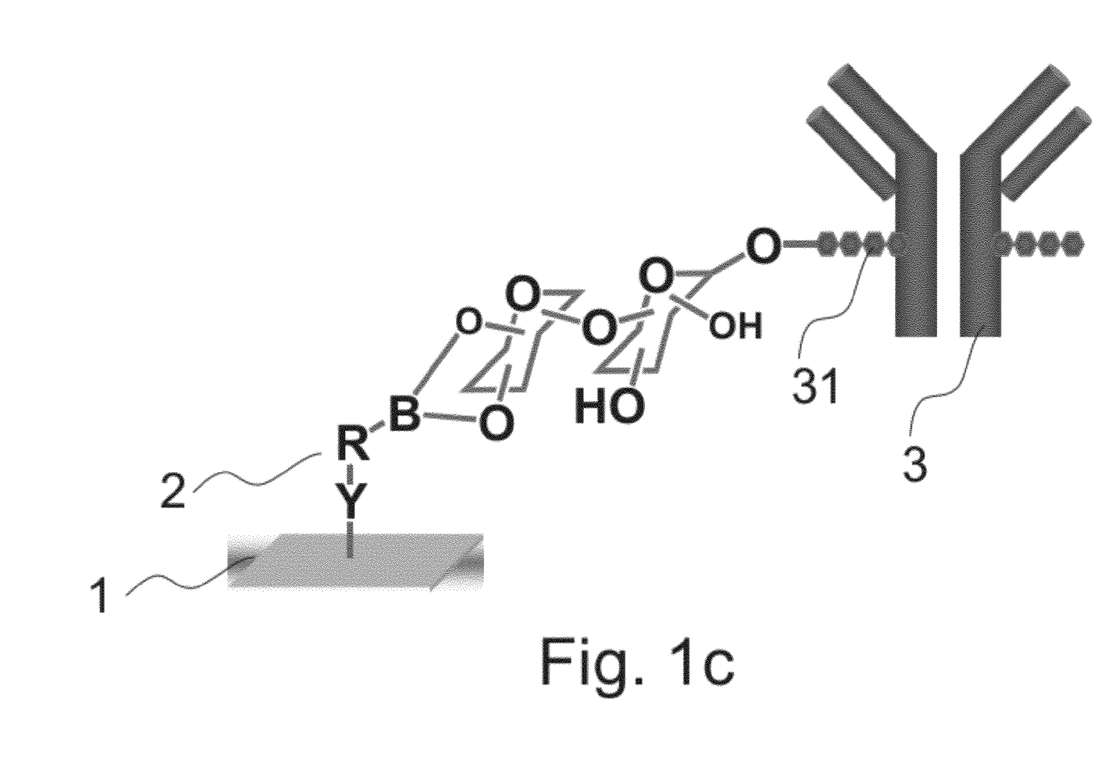

Here, as illustrated in examples, the two spatially adjacent hydroxyl groups of the carbohydrate chain 31 may be vicinal diols of adjacent carbon atoms (as illustrated in FIG. 1c) or two spatially verged hydroxyl groups due to spatial distribution of different carbon atoms.

It is understood that the protein may be an Fc-fusion protein that includes an Fc region with a carbohydrate chain for the immobilizing method of the present invention to be realized.

Figure 2A:
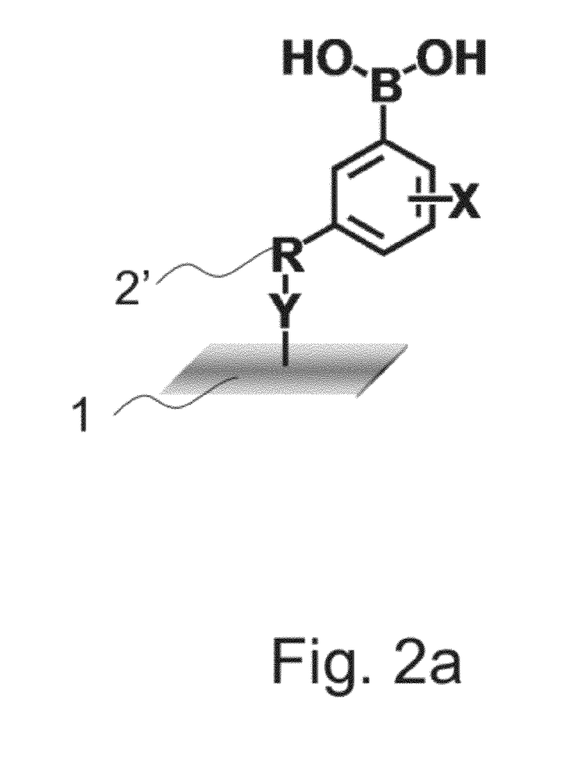
FIG. 2a and FIG. 2b are schematic diagrams illustrating a method for immobilizing glycoprotein according to another embodiment of the present invention.

FIG. 2a illustrates a method for immobilizing glycoprotein according to another embodiment of the present invention. First, a surface 1 is provided. A boronic acid 2' is then contacted to the surface 1, wherein the boronic acid 2' may be represented as Y—R—$C_6H_3X$—B—$(OH)_2$ and includes a phenylboronic acid ($C_6H_3$—(B—$(OH)_2$) with a boronic acid group B—$(OH)_2$, an auxiliary substituent X, a linker R, and a functional group Y. The auxiliary substituent X is linked to the phenylboronic acid. The linker R is linked to the phenylboronic acid. The functional group Y is bonded to the linker R and used for bonding to the surface 1. A glycoprotein containing an Fc region is contacted to the boronic acid at last. In this embodiment, the glycoprotein may be an antibody 3, for example.

To improve the binding, a secondary interaction is formed with the auxiliary substituent X of the boronic acid 2' to facilitate the immobilization of the antibody 3. The auxiliary substituent X may be hydrogen bond acceptor, covalent bond acceptor, chelator or so on, and the correspondent auxiliary may be hydrogen bond, covalent bond, chelation or so on. The carbohydrate chain 31 of the Fc region of the antibody 3 approach the boronic acid 2' through the aforementioned interaction with the auxiliary substituent X, and at least one hydroxyl groups of a carbohydrate chain 31 of the Fc region of the antibody 3 form a hemiboronate bond simultaneously with the boronic acid 2'. Two spatially adjacent hydroxyl groups of a carbohydrate chain 31 of the Fc region of the antibody 3 may also be facilitated to form a boronate bond with the boronic acid 2' by the second interaction.

The auxiliary substituent X may be a hydrogen bond acceptor. The hydrogen bond is formed with the interaction between the hydrogen bond donor, i.e. the hydroxyl groups in the carbohydrate chain 31 and the hydrogen bond acceptor, i.e. the auxiliary substituent X. The hydrogen bond acceptor may include an oxygen atom, a fluorine atom, a nitrogen atom or a substituent group comprising the aforementioned atoms.

The auxiliary substituent X may be a chelating group. The chelation is formed with the interaction between the chelation donor, i.e. the hydroxyl groups in the carbohydrate chain 31 and the chelation acceptor, i.e. the auxiliary substituent X. The chelation acceptor may include metal ion chelator such as nitrilotriacetic acid, pyridine, histidine or a substituent group comprising the aforementioned groups.

The auxiliary substituent X may be configured for improving boronic acid activity. The auxiliary substituent X may comprise a boronic acid binding facilitator such as an electron-withdrawing group based $pK_a$ reducer (e.g. a halide group, carboxyl group, nitrosyl group) or a boroxine inhibiting group (e.g. hydroxymethyl group) for maintaining boronic acid activity.

Figure 2B:
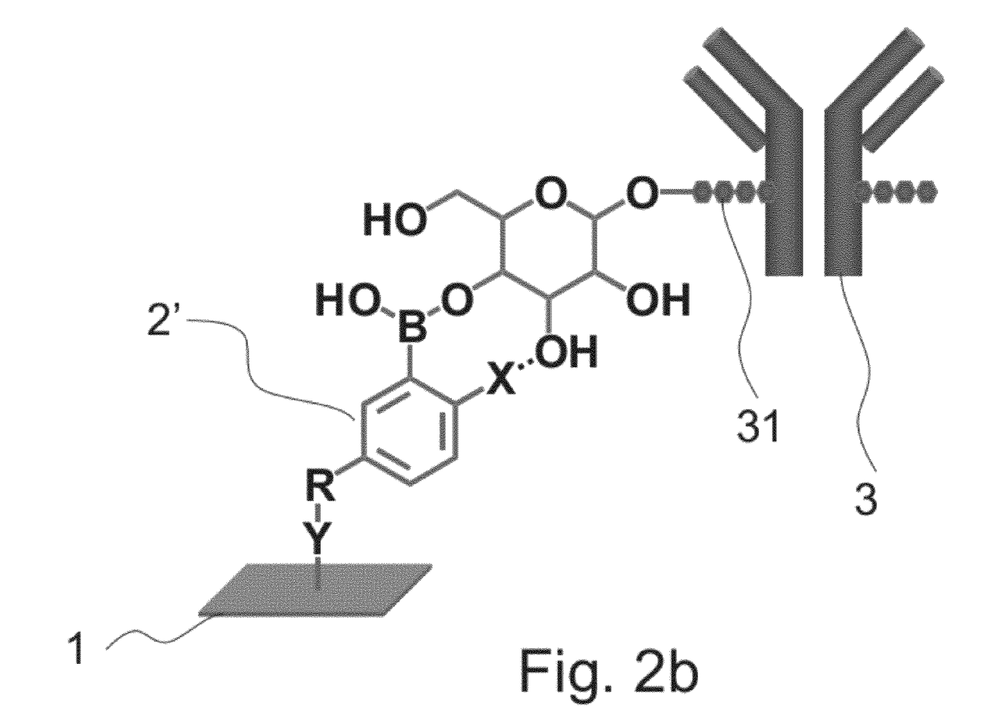

It is noted that the surface 1, the linker R, the functional group Y and the glycoprotein illustrated in FIG. 2b are similar with those in FIG. 1b. The detailed description thereof is not repeated.

The following descriptions of specific embodiments of the present invention have been presented for purposes of illustrations and description. They are not intended to be exclusive or to limit the invention to the precise forms disclosed, and obviously many modifications and variations are possible in light of the above teaching. It is intended that the scope of the invention be defined by the Claims appended hereto and their equivalents.

Figure 3:
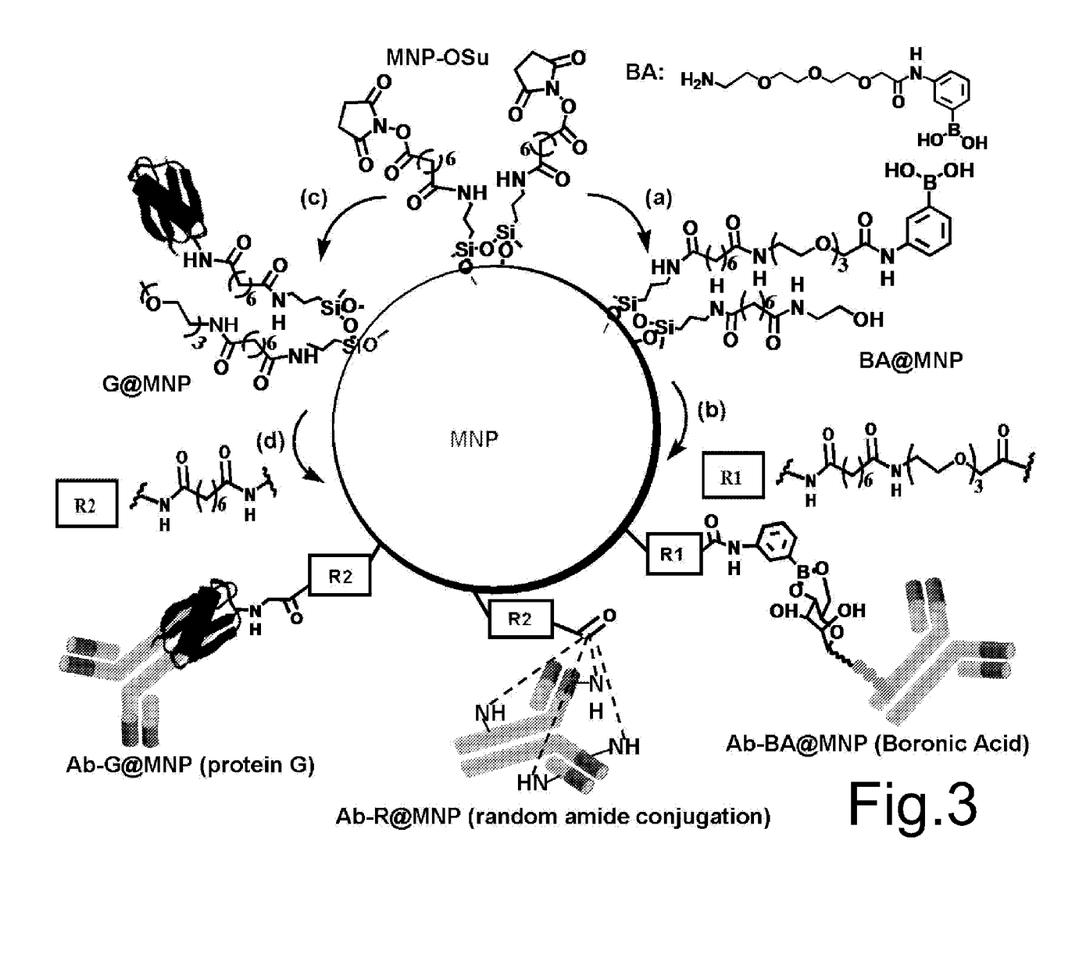
FIG. 3 is a schematic diagram illustrating a method for immobilizing glycoprotein according to another embodiment of the present invention.

Referring to FIG. 3, for comparing the activity differences caused by the present invention, three different antibody-conjugated MNPs (magnetic nanoparticles) were prepared, including random immobilization via amide bond formation (Ab-R@MNP), and oriented conjugation via protein G affinity (Ab-G@MNP), or via boronate formation (Ab-BA@MNP). Aminated MNP was used as the starting material and was incubated in the presence of bis N-hydroxysuccinimide ester (DSS) to generate the activated MNP-OSu, which was then conjugated with the antibody itself, protein G, and BA to yield Ab-R@MNP (non-oriented), G@MNP, and BA@MNP, respectively. For site-specific immobilization of antibody on MNPs, the G@MNP and BA@MNP were subsequently incubated with antibody for 12 hr at 4° C. followed by washing with phosphate-buffered saline three times. The resulting Ab-BA@MNP and Ab-G@MNP products exhibited oriented immobilization of the antibody via the Fc domain, which precludes steric hindrance of the antigen binding site.

Serum amyloid P component (SAP) was chosen as the model antigen for the comparison. Three antibody-conjugated nanoparticles, anti-SAP-R@MNP, anti-SAP-G@MNP, and anti-SAP-BA@MNP were prepared and then incubated with a SAP solution (12 nM).

To ensure fair comparison of the immuno-activity on the three immobilization methods, equal amount of antibody was used in each assay. Thus, a 1:1.7:1.2 weight ratio of anti-SAP-R@MNP:anti-SAP-G@MNP:anti-SAP-BA@MNP was used in parallel immunoassays, respectively based on the aforementioned principle. After antibody-antigen interaction and a series of washes to remove interferences, all antigen/antibody/MNP complexes were directly analyzed by matrix-assisted laser desorption/ionization time-of-flight mass spectrometry (MALDI-TOF MS). To quantitatively evaluate the MNP-bound antibody activities, 1 µL of myoglobin (designated as Myo, 1 µM) was spiked into the analyzed sample as an internal standard protein.

Figure 4A:
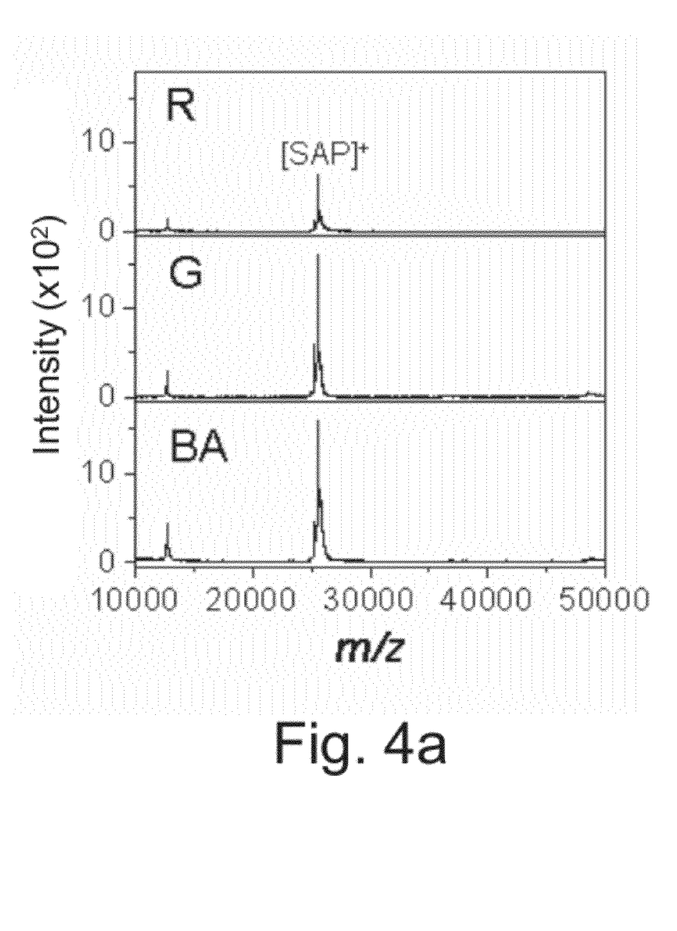
FIG. 4a to FIG. 4c are diagrams illustrating the experiment outcome of one example of the present invention and the conventional art.
Figure 4B:
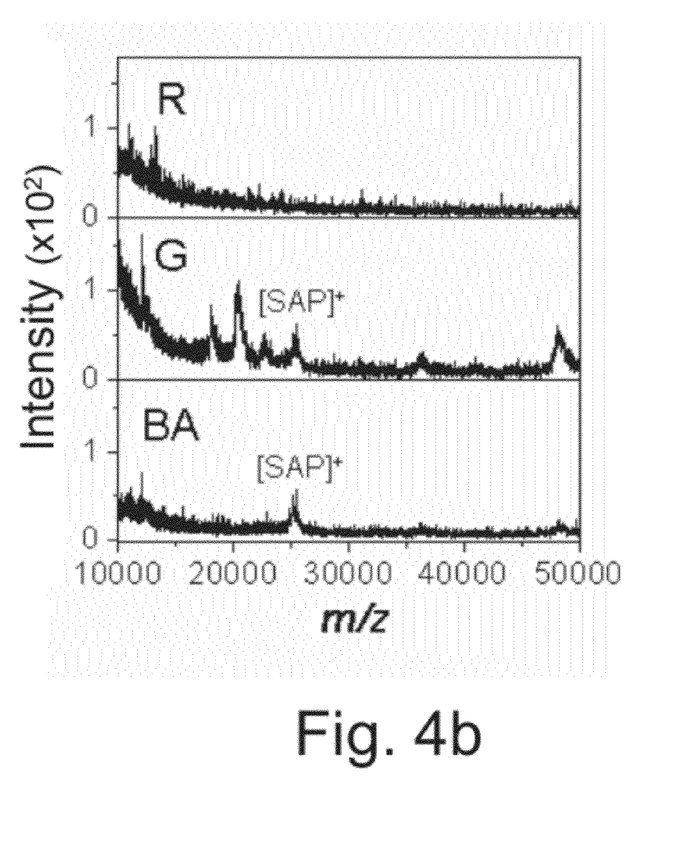
Figure 4C:
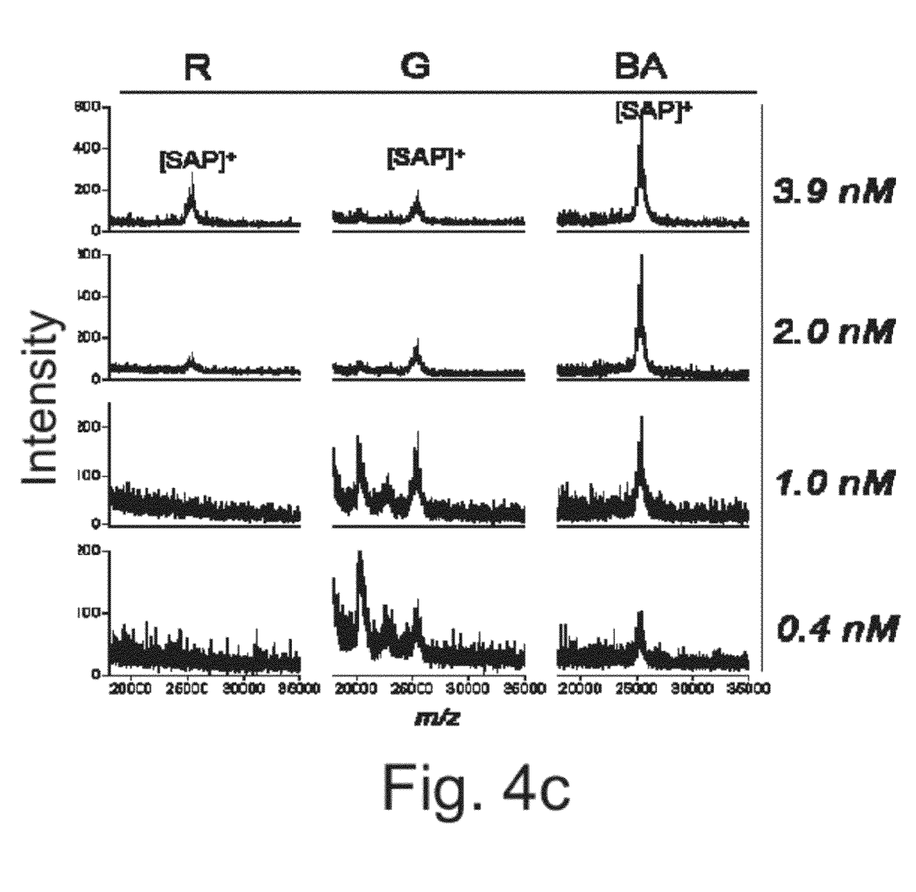

As illustrated in FIG. 4a, compared to the randomly conjugated anti-SAP-R@MNP, anti-SAP-G@MNP and anti-SAP-BA@MNP showed 5 times higher in detection sensitivity. The difference in capture efficiency was more dramatic when low antigen concentration was used (as illustrated in FIG. 4b and FIG. 4c). For example, the anti-SAP-R@MNP failed to detect SAP in a 0.4 nM solution, whereas both anti-SAP-G@MNP and anti-SAP-BA@MNP effectively extracted SAP at this low concentration.

Although the anti-SAP-G@MNP can retrieve SAP from more diluted SAP solution, it is noted that the non-covalent nature of the interaction between the anti-SAP and the protein G resulted in background interference in the mass spectrum (FIG. 4c). Therefore BA@MNP may be demonstrated as the more economic, efficient, and stable immunoprobe through site-specifically covalent conjugation for immobilizing protein, resulting in interference-free detection and better detection sensitivity.

Furthermore, the applicability of oriented site-specific immunoprobes for clinic diagnosis was examined. Three antibodies, anti-SAP, anti-C-reactive-protein (anti-CRP), and anti-serum amyloid A protein (anti-SAA), were conjugated with BA@MNP via site-specific boronate formation (capped with dextran) and subsequently used in multiplexed serum antigen profiling.

Figure 5A:
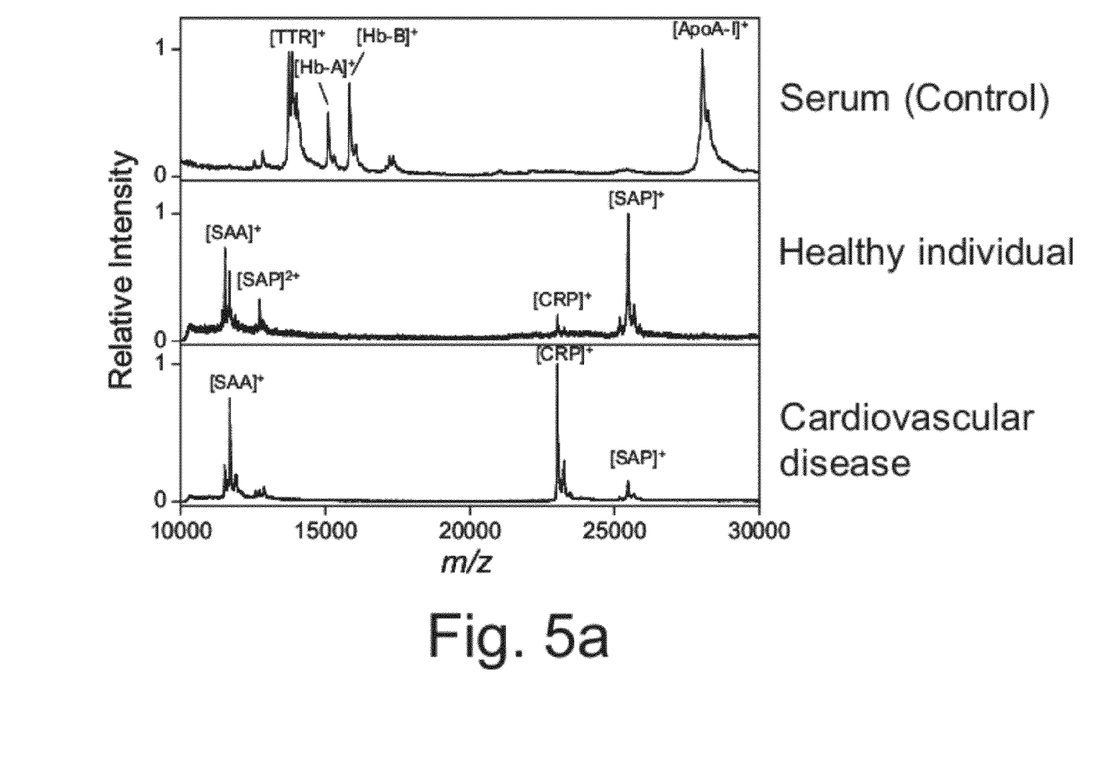
FIGS. 5a and 5b are diagrams illustrating the experiment outcome of one example of the present invention.

After determining the relative proportion of the three nanoprobes, 3.5-μl aliquots of a 1:4:2 weight ratio of anti-SAA-BA-dex@MNP:anti-CRP-BA-dex@MNP: anti-SAP-BA-dex@MNP were incubated with human serum samples from healthy subjects or from patients with cancer or cardiovascular diseases. Compared with the serum protein profiling in the upper panel illustrated in FIG. 5a, the three target antigens were successfully extracted from serum of a healthy individual without abundant protein interference (FIG. 5a, upper panel), demonstrating that the present invention is capable of providing simultaneous and specific multiple protein analysis.

Figure 5B:
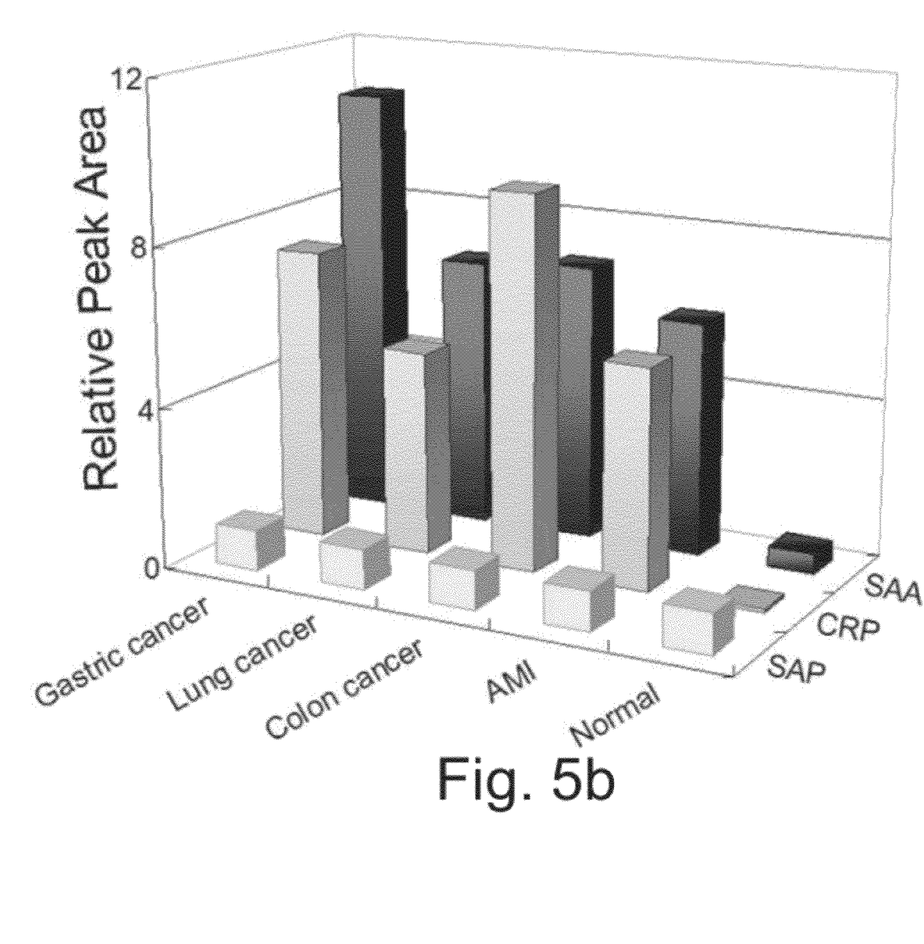

In addition, the nanoprobe immunoassay provided by the present invention revealed increased levels of CRP and SAA in serum from a cardiovascular disease patient (FIG. 5a, lower panel), consistent with parallel analysis by enzyme-linked immunosorbent assay (data not shown) and with literature reports. The nanoprobes were further applied to detect elevated antigen levels in serum samples from cancer patients, including those with gastric, lung, and colon cancers. After normalization of SAA and CRP signals to that of SAP which is stable in human serum both CRP and SAA were shown to be remarkably elevated in all cancer patient samples (FIG. 5b). The dramatic difference between SAP, SAA and CRP levels observed in our immunoassay among healthy subjects and patients clearly delineates the complexity of altered abundance in disease markers, an increased diagnostic accuracy can be achieved by the incorporation of multiple BA-orientated immunoprobes.

To sum up, glycoprotein may be immobilized via coupling mechanism between boronic acid and carbohydrates of Fc region and gain the advantages of site-specific and covalent protein immobilization without interfering the binding affinity of an antibody to antigen. The present invention may be applied to microarray chips or standard and microscale chromatography beads, and may lead to the development of other rapid and cost-effective high-throughput screening tools.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A method for immobilizing glycoprotein, comprising:
providing a surface;
contacting a boronic acid to the surface, wherein the boronic acid is represented by Y—R—B—(OH)$_2$ and includes a boronic acid group B—(OH)$_2$, a linker R, and a functional group Y, in which the boronic acid is bonded to the surface via the functional group Y; and
contacting a glycoprotein to the boronic acid, wherein two spatially adjacent hydroxyl group of a carbohydrate chain of the glycoprotein form a boronate ester with the boronic acid group to immobilize the glycoprotein.

2. The method as claimed in claim 1, wherein the linker R comprises an alkyl group, an alkoxy group, an alkyl ether group, an alkyl sulfide, a cycloalkyl group, a heterocyclyl group, an aryl group or a heteroaryl group.

3. The method as claimed in claim 1, wherein the boronic acid group comprises a phenylboronic acid.

4. The method as claimed in claim 3, wherein the phenylboronic acid comprises an auxiliary substituent.

5. The method as claimed in claim 4, wherein the auxiliary substituent comprises a boronic acid binding facilitator.

6. The method as claimed in claim 5, wherein the boronic acid binding facilitator comprises an electron-withdrawing group based pK$_a$ reducer.

7. The method as claimed in claim 5, wherein the boronic acid binding facilitator comprises a boroxine formation inhibitor.

8. The method as claimed in claim 4, wherein the auxiliary substituent comprises a second interaction group.

9. The method as claimed in claim 8, wherein the second interaction group comprises hydrogen bond acceptor.

10. The method as claimed in claim 9, wherein the hydrogen bond acceptor comprises an oxygen atom, a fluorine atom, a nitrogen atom or a substituent group comprising the aforementioned atoms.

11. The method as claimed in claim 8, wherein the second interaction group comprises a chelator.

12. The method as claimed in claim 8, wherein the second interaction group comprises a covalent acceptor.

13. The method as claimed in claim 3, wherein the linker R further comprises an amide group linking to the phenylboronic acid.

14. The method as claimed in claim 1, wherein the surface comprises a solid support, a nanoparticle or a biochip.

15. The method as claimed in claim 1, wherein the functional group Y is a member selected from the group consisting an amine, a hydrazide (—CO—NH—NH$_2$), an amine oxide (—O—NH$_2$), a thiol (—SH), an alkyne, an azide, a triaryl phosphine, an alkene, a diene, a cysteine, a thioester, a diazo, a diazirine, a benzophenone, and a diazonium.

16. The method as claimed in claim 15, wherein the boronic acid is bonded to the surface via Schiff base formation, amide bond formation, Staudinger ligation, 1,3-dipolar cycloaddition, Diels-alder [4+2] reaction, native chemical ligation, photo induced carbene immobilization, or photo induced nitrene immobilization.

17. The method as claimed in claim 1, wherein the glycoprotein comprises an antibody or an Fc-fusion protein.

18. The method as claimed in claim 1, wherein the carbohydrate chain is site specific.

19. The method as claimed in claim 1, wherein the boronate ester is formed with two spatially adjacent hydroxyl groups of the carbohydrate chain of the glycoprotein and the boronic acid group.

20. The method as claimed in claim 1 further comprising a step of providing a blocking agent to saturate the boronic acid that is not bonded with the glycoprotein.

21. The method as claimed in claim 20, wherein the blocking agent comprises a polyol or a diol.

22. The method as claimed in claim 21, wherein the blocking agent comprises a dextran.

* * * * *